United States Patent [19]

Marcus et al.

[11] Patent Number: 5,335,993
[45] Date of Patent: Aug. 9, 1994

[54] METHOD AND APPARATUS FOR THERMAL CONDUCTIVITY MEASUREMENTS

[75] Inventors: Sanford M. Marcus, Wilmington, Del.; Michael Reading, London, England

[73] Assignee: TA Instruments, Inc., New Castle, Del.

[21] Appl. No.: 85,646

[22] Filed: Jun. 30, 1993

Related U.S. Application Data

[63] Continuation-in-part of Ser. No. 844,448, Mar. 2, 1992, Pat. No. 5,224,775.

[51] Int. Cl.$^5$ .............................. G01N 25/20
[52] U.S. Cl. ............................ 374/11; 374/44; 374/33
[58] Field of Search ................... 374/10, 11, 12, 13, 374/14, 16, 31, 33, 43, 44, 179; 364/557

[56] References Cited

U.S. PATENT DOCUMENTS

| | | | |
|---|---|---|---|
| 2,975,629 | 3/1961 | Herbert . | |
| 3,263,484 | 8/1966 | Watson et al. | 374/11 |
| 3,271,996 | 9/1966 | Paulik et al. | 374/10 |
| 3,339,398 | 9/1967 | Barrall et al. | 374/11 |
| 3,360,993 | 1/1968 | MacMillan | 374/10 |
| 3,417,604 | 12/1968 | Bean et al. | 374/11 |
| 3,733,887 | 5/1973 | Stanley et al. | 374/44 |
| 3,789,662 | 2/1974 | Zettler et al. | 374/31 |
| 4,255,961 | 3/1981 | Biltonen et al. | 374/11 |
| 4,350,446 | 9/1982 | Johnson | 374/13 |
| 4,690,569 | 9/1987 | Veitch | 374/12 |
| 4,747,698 | 5/1988 | Wickramasinghe et al. | 374/124 |
| 4,783,174 | 11/1988 | Gmelin et al. | 374/11 |
| 4,812,051 | 3/1989 | Paulik et al. | 374/10 |
| 4,838,706 | 6/1989 | Coey et al. | 374/33 |
| 4,840,496 | 6/1989 | Elleman et al. | 374/124 |
| 4,859,078 | 8/1989 | Bowman et al. | 374/44 |
| 5,046,858 | 9/1991 | Tucker | 374/179 |
| 5,080,495 | 1/1992 | Hashimoto | 374/43 |
| 5,152,607 | 10/1992 | Ibar | 374/45 |
| 5,165,792 | 11/1992 | Crowe et al. | 374/10 |
| 5,224,775 | 7/1993 | Reading et al. | 374/11 |

FOREIGN PATENT DOCUMENTS 0051266 5/1982 European Pat. Off. .
0380414 8/1990 European Pat. Off. .

OTHER PUBLICATIONS

N. O. Birge and S. R. Nagel, "Specific-Heat Spectroscopy of the Glass Transition," Physical Review Letters, vol. 54, No. 25, Jun. 24, 1985, pp. 2674-2677.

N. O. Birge, "Specific-Heat Spectroscopy of Glycerol and Propylene Glycol Near the Glass Transition," Physical Review B., vol. 34, No. 3, Aug. 1, 1986, pp. 1631-1642.

N. O. Birge and S. R. Nagel, "Wide-Frequency Specific Heat Spectrometer," Rev. Sci. Instrum., vol. 58, Aug. 1987, pp. 1464-1470.

(List continued on next page.)

Primary Examiner—William A. Cuchlinski, Jr.
Assistant Examiner—G. Bradley Bennett
Attorney, Agent, or Firm—Kirkland & Ellis

[57] ABSTRACT

A method and apparatus for measuring the thermal conductivity of materials using modulated differential scanning calorimetry (MDSC). Two MDSC heat capacity measurements are made consecutively. One measurement is made under conditions which ensure obtaining a fairly accurate value for the heat capacity of the material ("quasi-ideal conditions"). Another measurement is made under conditions such that the measured effective heat capacity differs from the accurate value of the heat capacity due to thermal conductivity effects. Generally, the non-ideal conditions differ from the ideal conditions by one parameter, such as the size of the sample, the modulation frequency used to measure the heat capacity, or, for thin films, the presence or absence of a specimen on the thin film. The thermal conductivity of the material is then calculated from the difference between the heat capacity measured under quasi-ideal conditions and the effective heat capacity measured under non-ideal conditions.

34 Claims, 3 Drawing Sheets

OTHER PUBLICATIONS

R. Garcia, "Scanning Tunneling Microscopy in Biology: Changing the Pace," Microscopy and Analysis, Jul. 1991, pp. 27–29.

J. E. Graebner, "Modulated-Bath Calorimetry," Review of Scientific Instruments, Jun. 1989, pp. 1123–1128.

I. Hatta and A. J. Ikushima, "Studies on Phase Transitions by AC Calorimetry," Japanese Journal of Applied Physics, Nov. 1981, pp. 1995–2011.

M. Heitschold, P. K. Hansma, A. L. Weisenhorn, "Scanning-Probe-Microscopy and Spectroscopy in Materials Science," Microscopy and Analysis, Sep. 1991, pp. 25–27.

D. H. Jung, T. W. Kwon, D. J. Bae, I. K. Moon and Y. H. Jeong, "Fully Automated Dynamic Calorimeter," Meas. Sci. Technol., vol. 3, 1992, pp. 475–484.

S. MacPherson, "Atomic Resolution," Laboratory News, Mar. 19, 1990.

O. L. Mayorga, W. W. van Osdol, J. L. LaComba and E. Freire, "Frequency Spectrum of Enthalpy Fluctuations Associated with Macromolecular Transitions," Proc. Natl. Acad. Sci. U.S.A., vol. 85, Dec. 1988, pp. 9514–9518.

M. J. Miles, "The Application of STM/AFM to Biological Molecules,"Microscopy and Analysis, Jul. 1990, pp. 7–9.

H. S. Rade and F. Ringelmann, "Wechselstromkalorimetrie-Ein Empfindliches und Kontinuirlich Registrierendes Verfahren Zur Messung Spezifischer Warmen Kleiner Proben," Feinwerktechnik & Messtechnik, Jul. 1977, pp. 223–226.

A. Rosenowaig, "Photoacoustic Microscopy," International Laboratory, Sep./Oct. 1979, pp. 37–43.

P. F. Sullivan and G. Seidel, "Steady-State, AC-Temperature Calorimetry," Physical Review, vol. 173, No. 3, Sep. 15, 1968, pp. 679–685.

N. F. van Hulst and F. B. Segerink, "Optical Microscopy Beyond the Diffraction Limit," Microscopy and Analysis, Jun. 1992, pp. 21–23.

C. C. Williams and H. K. Wickramasinghe, "Photothermal Imaging with Sub-100-nm Spatial Resolution," Photoacoustic and Photothermal Phenomena Proceedings, pp. 364–368.

H. Yao and I. Hatta, "An AC Microcalorimetric Method for Precise Heat Capacity Measurement in a Small Amount of Liquid," Japanese Journal of Applied Physics, Jan. 1988, pp. 121–122.

Ulvac Sinku-Riko, Inc. product brochure ACC-1, "AC Calorimeter," publication date unknown, Catalog No. 8909-A13E/90.71000.

Ulvac Sinku-Riko, Inc. product brochure, "Thermal Constants Analyzer by AC Calorimetric Method," publication date unknown, Catalog No. 9010-P1TR1/90.10.3000.

Ulvac Sinku-Riko, Inc. product brochure ACC-VL1, "AC Calorimeter," publication date unknown, Catalog No. 9102-A24E.

Microscopy and Analysis, "Aris Scanning Tunneling Microscope," Jan. 1992.

Di product brochure, "Nanoscope II, Scanning Tunneling Microscope," publication date unknown.

Struers product brochure, "Welcome to the World of Atoms, Tunnelscope 2400," publication date unknown.

Struers product brochure, "Welcome to the World of Atoms, Tunnelscope 2400, Software Version 2.0," publication date unknown.

G. S. Dixon, S. G. Black, C. T. Butler and A. K. Jain, "A Differential AC Calorimeter for Biophysical Studies," Analytical Biochemistry 121, 1982, pp. 55–61.

J. Mitchell, J. Fisher, M. Nye, J. Redfern and D. Miller, "DSC: A new design for evaluating the thermal behavior of materials," International Laboratory, Feb. 28, 1991, pp. 44–48.

METHOD AND APPARATUS FOR THERMAL CONDUCTIVITY MEASUREMENTS

The present application is a continuation-in-part of application Ser. No. 07/844,448, filed on Mar. 2, 1992 (the "parent application"), now U.S. Pat. No. 5,224,775, which is expressly incorporated by reference herein.

BACKGROUND

1. Field of the Invention

The present invention relates to apparatus and methods using Modulated Differential Scanning Calorimetry ("MDSC") to measure the thermal conductivity of materials.

2. Background of the Invention

Thermal conductivity characterizes the ability of a material to conduct heat. Traditional methods for measuring the thermal conductivity of materials comprise imposing a temperature gradient upon a material of known geometry, and measuring the heat flow through the material. The heat flow is measured by, for example, measuring the temperature drop across a sheet of known thermal conductivity.

P. G. Knibbe, J. Phys. E: Sci. Instrum., vol. 20, pp. 1205–1211 (1987) describes a "hot wire" technique for measuring the thermal conductivity of a material. This technique uses a temperature-sensitive resistor wire embedded in a sample of the material. The resistor wire serves the dual function of supplying heat to the specimen, and measuring the temperature change at the wire. This rate of change is related to the thermal conductivity of the sample of the material.

D. G. Cahill and R. O. Pohl, Phys. Rev. B. vol. 35, p. 4067 (1987), and D. G. Cahill, Rev. Sci. Instrum. vol. 61(2), pp. 802–808 (1990), describe a "$3\omega$" technique for measuring thermal conductivity. This technique uses a temperature sensitive resistive metal film evaporated as a narrow line onto the surface of the sample to simultaneously heat the sample and detect the flow of heat away from the metal line. A current at angular frequency $\omega$ heats the metal line at a frequency of $2\omega$. Because the resistance of a metal increases with increasing temperature, and this temperature is modulated by the sample thermal conductivity, this produces a small oscillation in the resistance of the metal line, resulting in a voltage across the resistor at a frequency of $3\omega$. The thermal conductivity of the sample is then calculated from the amplitude of the $3\omega$ voltage oscillations.

J. H. Flynn and D. M. Levin, Thermochimica Acta, vol. 126, pp. 93–100 (1988), describes a thermal conductivity measurement method, suitable for measuring the thermal conductivity of sheet materials, based upon first-order transitions in a sensor material. A film of the sensor material is placed on a surface of the sheet material. The thermal conductivity measurement is made at the temperature at which the sensor material undergoes a first order transition. For example, if indium is used as the sensor material, the measurement is made at the melting point of indium, i.e., at the temperature at which indium undergoes a first order transition. The flow of heat into the sensor material must match the transition enthalpy. The thermal conductivity of the sheet material is obtained by comparing the data obtained with only the sensor material in the heater of a differential scanning calorimeter, to the data obtained with the sensor material on top of the sheet material in the differential scanning calorimeter.

These techniques are all subject to significant limitations. For example, the hot wire technique requires large samples, long times for the sample to come into equilibrium, and an additional long measurement period. The $3\omega$ technique requires a thin metal film in intimate contact with the sample, with fine electrical contacts to the film. The metal film must be thermally isolated from any heat sink, except for the sample being measured. The combination of film and sample is not mechanically robust, and is not readily separable so that other samples can be measured. The first order transition technique is restricted to the temperatures where materials are available with sharp first order transitions.

On the other hand, the present invention provides for quick measurements using small samples. The samples can be easily and rapidly changed. Furthermore, the measurement is not restricted to a set of discrete temperatures.

DEFINITIONS

"Thermal conductivity," as used herein, is the ratio of the heat flow per unit area in the sample to the temperature gradient in the sample.

"Heat sink compound," as used herein, is a paste with high thermal conductivity used to attach a sample to a heat source.

"Specific heat," as used herein, is the ratio of the change in heat content of a sample of uniform temperature to the product of the change in temperature of the sample and mass of the sample.

"Effective heat capacity," as used herein, is the ratio of heat flow into a sample to the product of the amplitude of the temperature modulation applied to the sample at the heat source and the angular frequency of the temperature modulation.

"Encapsulated sample," as used herein, is a flat thin sample surrounded by a thin high-thermal conductivity layer conforming to the shape of the sample.

"Unencapsulated thick sample," as used herein, is either (1) a sample in the form of a cylinder with flat parallel faces perpendicular to the axis, or (2) a right angle rectangular solid with parallel faces, the distance between the parallel faces being at least 1 mm.

"Cross-sectional area," as used herein, is the area of a face on the unencapsulated thick sample.

"Quasi-ideal conditions," as used herein, are conditions for measuring the heat capacity of a material using modulated differential scanning calorimetry such that a fairly accurate value for the heat capacity of the material is obtained;

"Non-ideal conditions," as used herein, are conditions for measuring the heat capacity of a material such that thermal conductivity effects have a significant effect on the heat capacity measurement, such that the measured effective heat capacity deviates from the heat capacity measured under quasi-ideal conditions.

"Variable parameter," as used herein, is a parameter characterizing the difference between the quasi-ideal and non-ideal conditions. The variable parameter may be, for example, the dimensions of the sample, the modulation frequency used in the MDSC measurement, or the modulation amplitude used in the MDSC measurement.

SUMMARY OF THE INVENTION

The present invention uses MDSC to measure the thermal conductivity of materials. Two MDSC heat capacity measurements are made consecutively. One measurement is made under conditions which ensure obtaining a fairly accurate value for the heat capacity of a sample ("quasi-ideal conditions"). A second measurement is made under conditions wherein the measured effective heat capacity deviates from the true heat capacity of the sample due to thermal conductivity effects ("non-ideal conditions"). Generally, the non-ideal conditions differ from the quasi-ideal conditions by one parameter, e.g., the size of the sample, the modulation frequency used, the modulation amplitude, and (for thin films), the presence or absence of a specimen on the thin film. The thermal conductivity of the material is then calculated from the difference between the measured heat capacity under quasi-ideal conditions and the measured effective heat capacity under non-ideal conditions.

In a first embodiment of the present invention, the variable parameter is the size of the sample. A small sample and a large sample of the material whose thermal conductivity is to be determined are prepared. For example, the large sample may be a circular cylinder having a given height, whereas the small sample could be a disc of the sample material (i.e., a thin cylinder). The specific heat of the small sample and the effective heat capacity of the large sample are then measured using MDSC. The thermal conductivity of the material is then calculated from the measured values of specific heat and effective heat capacity.

Thus, in the first embodiment of the present invention, a first sample (the small sample) of the material to be measured is prepared as a wafer with a thickness of 1 mm or less, encapsulated in a thin conforming high thermal conductivity material (the "encapsulated sample"). The wafers are typically circular discs, although wafers having other shapes could be used. A second sample (the large sample) of the material is prepared as a right angle cylinder with parallel and flat top and bottom surfaces, the height of the cylinder being at least 1 mm (the "unencapsulated sample"). The cylinder typically has a circular cross-section. However, cylinders with other cross-sections, e.g., square, rectangular, or oval, may also be used. The encapsulated sample is now placed in a differential scanning calorimeter (a "DSC") on the sample position. A matching amount of the encapsulating material prepared as a wafer is placed on the reference position of the DSC.

The specific heat of the encapsulated sample is then measured using the modulated DSC procedure described in the parent application. The encapsulated sample and matching encapsulating material are then removed from the DSC and the unencapsulated sample is placed on the sample position. The heat capacity of the unencapsulated sample is then measured. The dimensions of the unencapsulated sample and its density are then measured. The thermal conductivity of the material is then calculated from the measured heat capacity, specific heat, sample dimensions, sample density and the angular frequency of the applied temperature oscillations, as described below.

The heat flow equation is derived from the one-dimensional thermal diffusivity equation, with an oscillatory temperature of a given amplitude and angular frequency applied to one surface of the sample. The sides and opposite face of the sample are assumed to be thermally insulated. This general solution is simplified by assuming that the diffusion length in the sample is short compared to the sample thickness. The thermal conductivity of the sample is calculated from this approximation, as described below.

A second embodiment of this invention improves the accuracy of the measurement by accounting for the finite heat flow external to the sample. The measurements and calculation of the thermal conductivity are carried out, as described for the first embodiment, on a sample of known thermal conductivity. The values of the measured and the known thermal conductivities are used to calculate a correction factor. The correction factor can then be applied to obtain a more accurate measurement of the thermal conductivity of samples having similar dimensions and measured under similar conditions. The second embodiment provides a more accurate thermal conductivity measurement because it accounts for the heat transmitted through the gas surrounding the sample.

A third embodiment of this invention is used to measure the thermal conductivity of films or of liquid samples. For thin films, a sample of the film to be measured is placed on the sample position of the DSC. A matching film of the same material is placed on the reference position. A specimen, of known weight and cross-section, is mounted on the top surface of the film, at the sample position. The effective heat capacity of the specimen is then measured. The thermal conductivity of the film is then obtained from the known heat capacity of the specimen, the measured effective heat capacity of the specimen, and the thickness of the film. Alternatively, the heat capacity of the specimen (instead of being "known," i.e., obtained from the published literature) could be measured first by placing the specimen in the sample position of the MDSC (without the sample of the thin film material at either the sample or reference positions of the MDSC), and then measuring the heat capacity of the specimen using the MDSC technique. This latter approach requires an additional measurement, but in some cases may have the advantage of being insensitive to instrumental artifacts.

For liquids, the same basic approach is used, except that the liquid is placed in a crucible, and the specimen must be supported on top of the liquid.

The equation used for calculating the thermal conductivity of the film or the liquid is derived from the one dimensional thermal diffusivity equation with one surface of the film held at a temperature oscillating at a given amplitude and angular frequency. The opposite surface is in contact with a material of known heat capacity per unit area. An approximate solution is obtained, assuming that the diffusion length is long compared to the film thickness.

A fourth embodiment of the present invention, the two-frequency technique, uses a single sample, instead of two samples of different thicknesses. The heat capacity of the sample is measured at two different modulation frequencies. At low frequencies, the measured effective heat capacity is very close to the true heat capacity. However, at higher modulation frequencies, the measured effective heat capacity deviates to a greater degree from the true heat capacity. The thermal conductivity of the material can then be calculated by comparing the heat capacity at high-frequencies to the heat capacity at low frequencies.

An object of the present invention is to provide a procedure and apparatus for rapidly measuring the thermal conductivity of materials continuously as a function of temperature, from subambient temperatures to moderately high temperatures.

Another object of the present invention is to provide a procedure and apparatus for using modulated DSC to measure the thermal conductivity of bulk materials.

Another object of the present invention is to provide a procedure and apparatus for using modulated DSC to measure the thermal conductivity of thin films or liquids.

Another object of the present invention is to provide a procedure and apparatus for measuring the thermal conductivity of materials using small samples.

Another object of the present invention is to provide a procedure and apparatus for measuring the thermal conductivity of materials having a wide range of thermal conductivity values.

Another object of the present invention is to provide a procedure and apparatus for measuring the thermal conductivity of materials without requiring the use of special accessories, specialized equipment, or special expertise, and without requiring any modifications to the standard MDSC apparatus.

Another object of the present invention is to provide a procedure and apparatus that can be used to measure the thermal conductivity of both liquids and solids.

Another object of the present invention is to provide a thermal conductivity measuring apparatus wherein measurement parameters such as temperature, scan rate, period, and amplitude can be easily changed.

Another object of the present invention is to provide a procedure and apparatus wherein the thermal conductivity of a sample of material could be measured using a small temperature difference between the sample and the environment.

DERIVATION OF THE THERMAL CONDUCTIVITY EQUATIONS MAKING USE OF MODULATED DSC

One-Dimensional Calculation

The temperature distribution along a rod in response to a periodic temperature variation applied to one end of the rod is given by:

$$T(x,t) = T(x)\omega^{i\omega t}$$

where:

$$T(x) = ae^{-\sqrt{\frac{i\omega}{\alpha}}x} + be^{+\sqrt{\frac{i\omega}{\alpha}}x}$$

and where:
$\omega$ is the angular frequency of the periodic temperature variation;
$\alpha$ is the diffusivity constant of the rod; and
a and b are constants determined by the boundary conditions.

The boundary conditions which determine a and b are:
$T(0) = T_0$ (the amplitude of the temperature oscillation at the base of the rod, i.e., at $x=0$);
$(dT/dx)_{x=L} = 0$ (no heat flow through the end of the rod, i.e., no heat flow at $x=L$).

The heat flow $dQ/dt$ into the base of the rod can be determined from the temperature distribution along the rod, using the relationship:

$$\left(\frac{dQ}{dt}\right)_{x=0} = -KA\left(\frac{dT}{dx}\right)_{x=0}$$

where:
K is the thermal conductivity of the rod; and
A is the cross-sectional area of the rod.

The amplitude of the heat flow along the rod is a function of the thermal and physical parameters of the rod. Multiplying the heat flow by its complex conjugate to obtain the heat flow amplitude, the following relationship is obtained:

$$\left|\frac{dQ}{dt}\right|^2 = 2(AT_0 K\Lambda)^2 \left(\frac{1 - (2e^{2\Lambda L})\cdot\cos(2\Lambda L) + e^{4\Lambda L}}{1 + e^{2\Lambda L}\cdot\cos(2\Lambda L) + e^{4\Lambda L}}\right)$$

and:

$$\frac{\left|\frac{dQ}{dt}\right|^2}{\omega^2 T_0^2} = C^2$$

where:
K is the thermal conductivity;
$|dQ/dt|$ is the heat flow amplitude;
$\omega$ is the angular frequency;
$\rho$ is the sample density;
C is the heat capacity;
$C_p$ is the sample specific heat;
$\Lambda^2 = \omega\cdot\rho\cdot C_p/2K$;
$T_o$ is the amplitude of the temperature modulation;
L is the length of the rod; and
A is the area of the cross section of the rod.

For the condition $e^{4\Lambda L} \gg 1$ the equation reduces to:

$$\left|\frac{dQ}{dt}\right|^2 = \omega\cdot\rho\cdot C_p\cdot T_0^2\cdot A^2\cdot K$$

Re-writing this equation to calculate thermal conductivity:

$$K = \frac{\left(\frac{dQ}{dt}\right)^2}{\omega\cdot\rho\cdot C_p\cdot T_0^2 A^2}$$

$$= \frac{\omega\cdot C^2}{\rho\cdot C_p\cdot A^2}$$

where $$C = \frac{\left|\frac{dQ}{dt}\right|}{\omega\cdot T_0}$$

Correction Factor

The one-dimensional calculation does not take into account heat flow through the gas surrounding the rod. The following calculation provides a method for accounting for this heat flow to first order. The method uses a measurement on a material having a known thermal conductivity to obtain a correction factor. The correction factor can then be applied to similar materials having similar dimensions and measured under similar experimental conditions.

Assuming that the heat flow into the gas surrounding the rod is proportional to the temperature gradient on the sample surface near the sample base:

$$T(x) = T_0 e^{-x\sqrt{\frac{\omega \cdot \rho \cdot C_p}{K_t}}}$$

where:
T(0) is the temperature at the base of the sample;
$\omega$ is the modulation angular velocity;
$\rho$ is the sample density;
$C_p$ is the sample specific heat; and
$K_t$ is the sample thermal conductivity.

The temperature gradient (dT/dx) in the vicinity of the sample base is proportional to:

$$\frac{dT}{dx} \propto \sqrt{\frac{\omega \rho C_p}{K_t}}$$

Assuming that the heat flow $(dQ/dt)_e$ through the gas is proportional to the gradient we have:

$$\left(\frac{dQ}{dt}\right)_e = RAT_0 \cdot \sqrt{\frac{\omega \rho C_p}{K_t}}$$

R is a scale factor that is dependent on the gas surrounding the sample, the dimensions of the sample and the run conditions. It is constant for a series of samples of the same dimensions under the same experimental conditions.

The total heat flow, consisting of the sum of the heat flow through the sample and through the gas, is used to calculate the measured effective thermal conductivity K, from the formula derived above:

$$K = \frac{\left(\frac{dQ}{dt}\right)^2}{A^2 \omega \rho C_p T_0^2}$$

where:
$T_o$ is the temperature modulation amplitude;
$|dQ/dt|$ is the measured amplitude of the modulated heat flow; and
A is the cross-section area of sample.
Therefore:

$$\frac{K_t}{K} = \frac{\left|\frac{dQ}{dt}\right|_t^2}{\left|\frac{dQ}{dt}\right|^2}$$

$$= \frac{\omega \rho C_p A^2 T_0^2 K_t}{(\sqrt{\omega} \, \rho C_p A^2 T_0^2 K_t + R \cdot \sqrt{\omega \rho C_p + K_t})^2}$$

where $|dQ/dt|_t$ is the heat flow through the sample and $|dQ/dt|$ is the measured heat flow.

Rewriting we have:

$$R = \sqrt{K_t K} - K_t$$

Thus R can be computed from the values of K and $K_t$.

Consequently, if a sample of known thermal conductivity $(K_t)$ is measured, thereby determining its effective thermal conductivity (K), the correction factor R can be calculated. The calculated value of the correction factor can then be applied to subsequent measurements, to compute the true thermal conductivity from the measured effective thermal conductivity, using the following equation:

$$K_t = \frac{K - 2R + \sqrt{K^2 - 4RK}}{2}$$

where R is the previously calculated correction factor and K is the measured effective thermal conductivity of the sample.

The Two-Frequency Technique

The two-frequency technique is implemented at a high frequency at which the high frequency equation:

$$K = \frac{\omega C^2}{\rho C_p A^2}$$

applies, i.e., at a frequency such that $e^{4\Lambda L} \gg 1$, and at a low frequency at which $e^{4\Lambda L}$ is not much greater than 1.

Therefore, the equations:

$$\left|\frac{dQ}{dt}\right|^2 = 2(\Lambda T_0 K A)^2 \left(\frac{1 - (2e^{2\Lambda L}) \cdot \cos(2\Lambda L) + e^{4\Lambda L}}{1 + e^{2\Lambda L} \cdot \cos(2\Lambda L) + e^{4\Lambda L}}\right)$$

and:

$$C^2 = \frac{\left|\frac{dQ}{dt}\right|^2}{\omega^2 T_0^2}$$

must be used at the low frequency to calculate C. The exponential terms can be approximated as second order polynomials. The value of C calculated at the low frequency is divided by the mass of the sample to obtain the specific heat of the sample:

$$C_p = \frac{C}{M}$$

This value of $C_p$ can then be used for $C_p$ in the high frequency equation. The value obtained for the measured effective heat capacity at the high frequency modulation can then be used for C in the high frequency equation to obtain the thermal conductivity K.

DETAILED DESCRIPTION OF THE INVENTION

Figure 1:
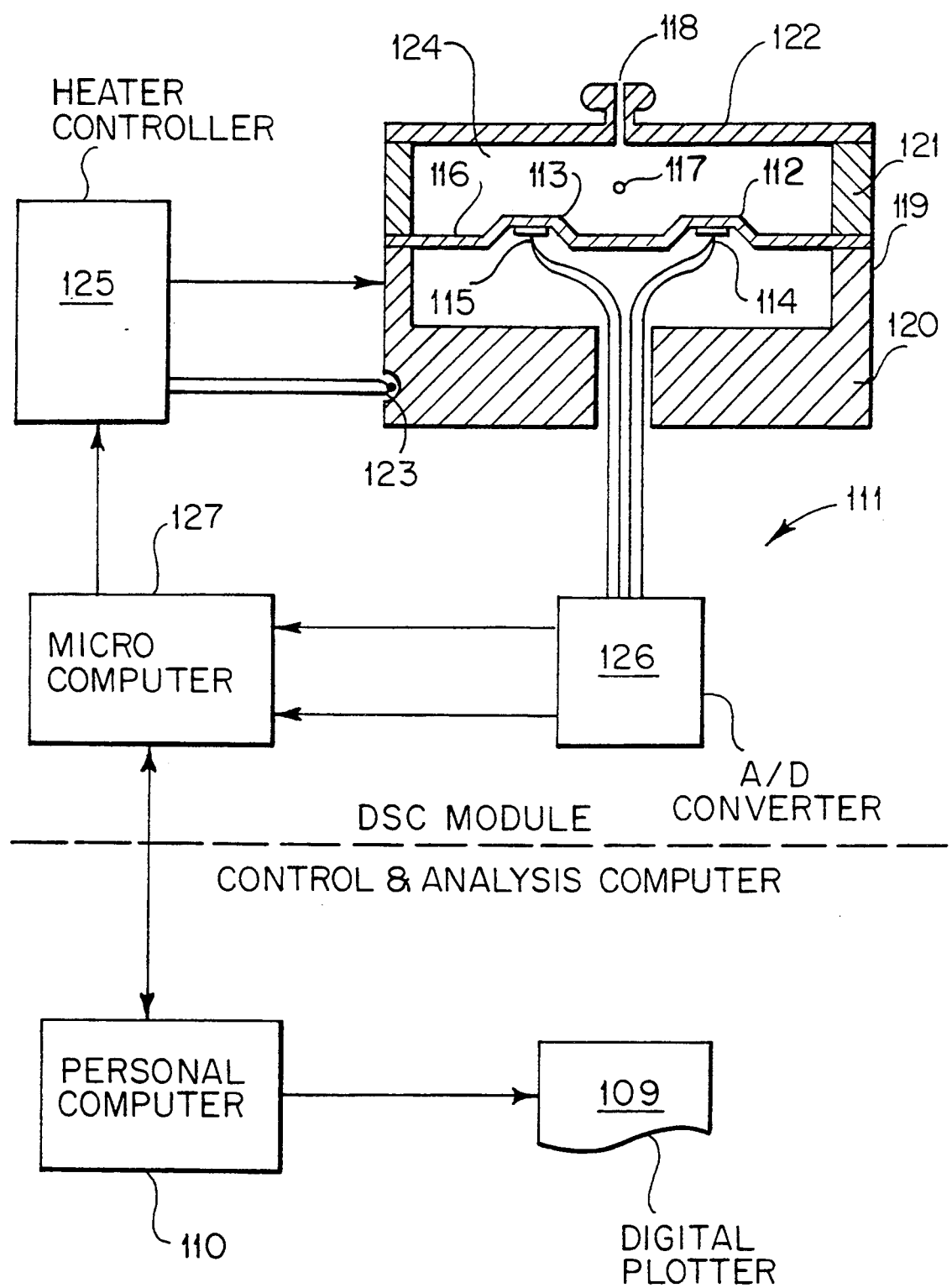
FIG. 1 is a schematic representation of the apparatus used to measure the thermal conductivity of materials according to the present invention.

FIG. 1 is a schematic representation of the MDSC apparatus used to measure the thermal conductivity of materials according to the present invention. FIG. 1 shows an MDSC apparatus 111 comprising sample position 112; reference position 113; sample temperature thermocouple 114; reference temperature thermocouple 115; thermoelectric disc 116; purge gas inlet 117; a purge gas outlet 118; electric furnace 119 which comprises silver block heater 120, silver ring 121, silver lid 122, and heater thermocouple 123; furnace chamber 124; heater controller 125; analog-to-digital converter 126; and microcomputer 127. FIG. 1 also shows personal computer 110 and digital plotter 109. Modulated differential scanning calorimeter 111 measures the heat flow difference between sample position 112 and reference position 113 which are supported by a thermoelectric disc 116 inside a closed furnace chamber 124. Thermoelectric disc 116 serves as the major heat flow path for transferring heat from furnace 119 to sample position 112 and reference position 113. The disc is also used as a common material of the differential thermocouple for measuring the temperature difference between the sample and reference positions. Microcomputer 127 receives differential temperature and sample temperature from sample thermocouple 114 and reference thermocouple 115 via analog-to-digital converter 126. Microcomputer 127 also controls the temperature of the furnace 119 by controlling the power to the furnace using heater controller 125. In the preferred embodiment of the present invention, the temperature of the furnace is controlled by microcomputer 127. However, the present invention can be practiced using any combination of computers, hardware and operator control. Personal computer 110 and digital plotter 109 are used to analyze, store, display and plot the analytical results. A purge gas is usually introduced via the purge gas inlet. The purge gas can be a gas that reacts with constituents of the sample being analyzed, or it can be an inert gas, i.e., a gas that does not react with the sample used to prevent reactions with air. Typical purge gases include dry air, oxygen, nitrogen, argon, helium, carbon monoxide and carbon dioxide.

The present invention is practiced by programming microcomputer 127 and personal computer 110 to carry out the procedures outlined below for each of the preferred embodiments of the invention.

Uncorrected Thermal Conductivity Measurements in Bulk Samples

In the first embodiment of the present invention, the thermal conductivity of a bulk material can be measured using the following procedure:

1. Prepare a first sample of the material (for use as the encapsulated sample) in the form of a disc. A typical disc may be 0.5 mm thick and 6 mm in diameter.

2. Weigh the first sample.

3. Encapsulate the first sample in a DSC sample pan (e.g., aluminum DSC sample pans), with cover.

4. Choose another sample pan with cover of the same weight as the DSC sample pan and crimp the second sample pan.

5. Prepare a second sample of the material (for use as the unencapsulated sample) in the form of a uniform right circular cylinder. The cylinder should have the same diameter as the disc. A typical cylinder may be approximately 3 mm long and 6 mm in diameter.

6. Measure the length and diameter of the second sample, and calculate the volume of the second sample.

7. Weigh the second sample.

8. Calculate the density of the second sample.

9. Place the encapsulated sample on the sample position of a MDSC cell, which is part of an MDSC system, described in the parent application, and place the matching crimped pan on the reference position of this cell.

10. Place the system in the MDSC mode, wherein the modulation temperature amplitude and the heat capacity signal are saved to memory.

11. Select a temperature at which to run the measurement, and a modulation amplitude, waveform and frequency, as described in the parent application.

12. Run an MDSC measurement isothermally, as described in the parent application, at the selected temperature, and according to the selected modulation amplitude, waveform and frequency. Typically, the measurement may be run at room temperature, with a sinusoidal modulation, a modulation period of 80 sec (i.e., a modulation frequency of 0.0125 sec$^{-1}$) and a modulation amplitude of $\pm 1°$ C., for 30 minutes.

13. Allow the modulation temperature amplitude to stabilize, then analyze the data for specific heat over a predetermined period. Typically, measurements are made at intervals of 30 minutes, using that fraction of the 30 minutes during which the modulation temperature amplitude has stabilized.

14. Remove the encapsulated sample and matching pan from the MDSC cell.

15. Prepare two discs from a thin sheet of smooth foil, e.g., 3 mils-thick aluminum foil 6 mm in diameter.

16. Attach one foil to the unencapsulated sample with a thin layer of heat sink compound by spreading a thin layer of the heat sink compound on one of the flat surfaces of the cylinder and pressing, with a sliding motion, the cylinder onto the foil, with the foil placed on a flat surface, and then removing any excess heat sink compound.

17. Place a thin layer of heat sink compound uniformly over the sample position of the cell and place an equal amount of heat sink compound over the reference position.

18. Mount the unencapsulated sample on the sample position of the cell, with foil side down, by pressing down with a sliding motion.

19. Mount the other foil disc on the unencapsulated sample, by pressing down on top surface of the foil with a flat instrument.

20. Run an MDSC measurement isothermally, as described in the parent application, using the experimental conditions selected in step 11.

21. Using the MDSC modulation analysis program, analyze the data for heat capacity at, e.g., intervals of 30 minutes, using that fraction of the 30 minutes during which the modulation temperature amplitude has stabilized.

22. Finally, calculate the thermal conductivity (K) of the material using the following equation and measured parameters:

$$K = (\omega \cdot C^2)/(C_p \cdot \rho \cdot A^2)$$

where:
A is the sample cross section area;
$\rho$ is the sample density;
$C_p$ is the sample specific heat (J/g °C.); and
C is the measured effective heat capacity (J/ °C.).
$\omega$ = angular frequency of modulation.

The procedure described above in steps 1–22 may be applied sequentially at a series of temperatures, to obtain the thermal conductivity of a material as a function of temperature. The dimensions of the materials would, of course, have to be measured at each temperature in order to obtain the most accurate thermal conductivity measurements possible. However, if the dimensions change only slightly as a function of temperature, the thermal expansion of the materials can be ignored.

Corrected Thermal Conductivity Measurements in Bulk Samples

The second embodiment of the present invention uses steps 1–22 to measure the thermal conductivity of a material having a known thermal conductivity, and thus obtain a correction factor to account for thermal conductivity through the gas surrounding the sample.

1–22. Measure the thermal conductivity of a sample of the material following the procedure described in steps 1–22 of the first embodiment.

23. Select a material having known thermal conductivity, and measure its thermal conductivity using steps 1–22, above, using a sample of the known material having similar dimensions to the sample of the unknown material being measured. Use the same experimental conditions and parameters as in steps 1–22.

24. Determine the correction factor R, using the following equation:

$$R = \sqrt{K_t \cdot K} - K_t$$

where:
K is the measured thermal conductivity;
$K_t$ is the true thermal conductivity; and
R is the correction factor.

25. Using the measured value of thermal conductivity of the sample calculated in step 22, substitute into the following equation to calculate the corrected value of thermal conductivity:

$$K_t = \frac{(K - 2R + \sqrt{K^2 - 4RK})}{2}$$

As discussed above with reference to the first embodiment of the invention, this procedure can be repeated sequentially at a series of temperatures to obtain a corrected value of the thermal conductivity as a function of temperature.

Thermal Conductivity Measurements in Thin Films

The third embodiment of the present invention uses MDSC to measure the thermal conductivity of thin films.

1. Make a cylinder. Typically, the cylinder is an aluminum cylinder 0.3 to 0.5 cm in diameter and 0.2 to 0.4 cm long.

2. Place a thin layer of heat sink compound uniformly over the sample position of the cell and place an equal amount of heat sink compound over the reference position.

3. Place the cylinder on the sample position, pressing the cylinder down with a sliding motion.

4. Measure the heat capacity of the cylinder isothermally at room temperature, at a predetermined modulation period and modulation amplitude. For example, the modulation period could be 80 sec, with a modulation amplitude of $\pm 1°$ C. over an interval of 30 minutes.

5. Remove the cylinder from the sample position.

6. Punch out two, e.g., 6 mm diameter discs of the thin film.

7. Attach these discs to the sample and reference positions, pressing down on the top surface of the films with a flat instrument.

8. Attach the cylinder to the top surface of the film at the sample position, pressing down on the film with a flat instrument.

9. Measure the effective heat capacity of the cylinder using MDSC, as described in the parent application, isothermally at room temperature, using the same modulation parameters as in step 4 above.

10. Substitute these two heat capacity values, film thickness, angular frequency and cylinder cross section area into the following equation to obtain the thermal conductivity of the film:

$$K = \frac{\omega C_{true} L}{A} \left( \frac{1}{\left(\frac{C_{true}}{C_{eff}}\right)^2 - 1} \right)^{\frac{1}{2}}$$

where:
$\omega$ is the angular frequency of the modulation;
L is the film thickness;
A is the cross section of the cylinder;
$C_{true}$ is the heat capacity of the cylinder directly attached to the sample position; and
$C_{eff}$ the measured effective heat capacity of the cylinder when attached to the sample position through the film.

As discussed above with reference to the first and second embodiments of the invention, this procedure can be repeated sequentially at a series of temperatures to measure the thermal conductivity of thin films as a function of temperature.

Further Embodiments

Figure 4A:
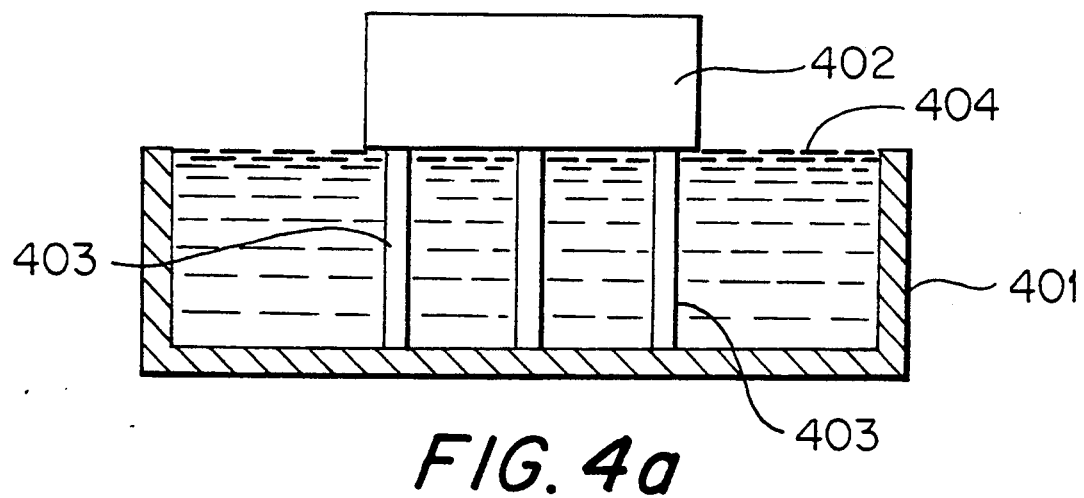
FIGS. 4a, 4b and 4c are schematic diagrams of different configurations that may be used to measure the thermal conductivity of liquids.
Figure 4B:
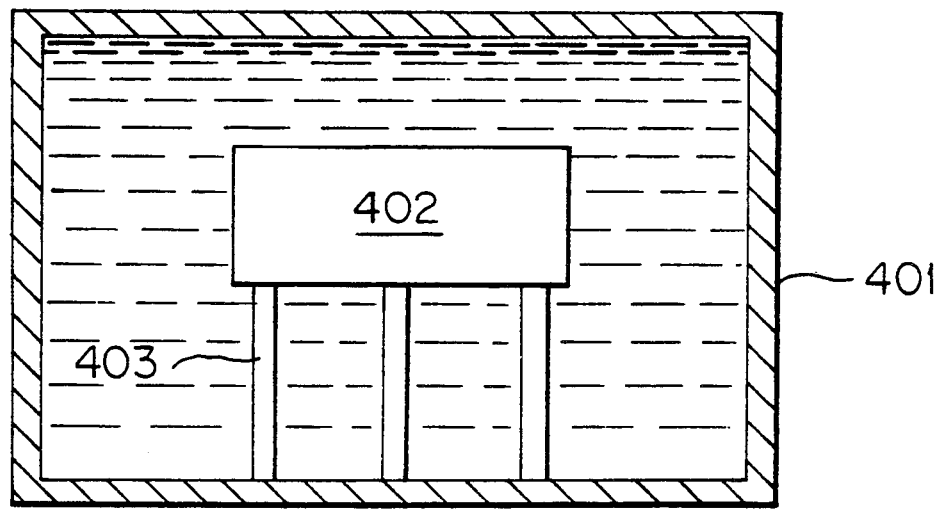
Figure 4C:
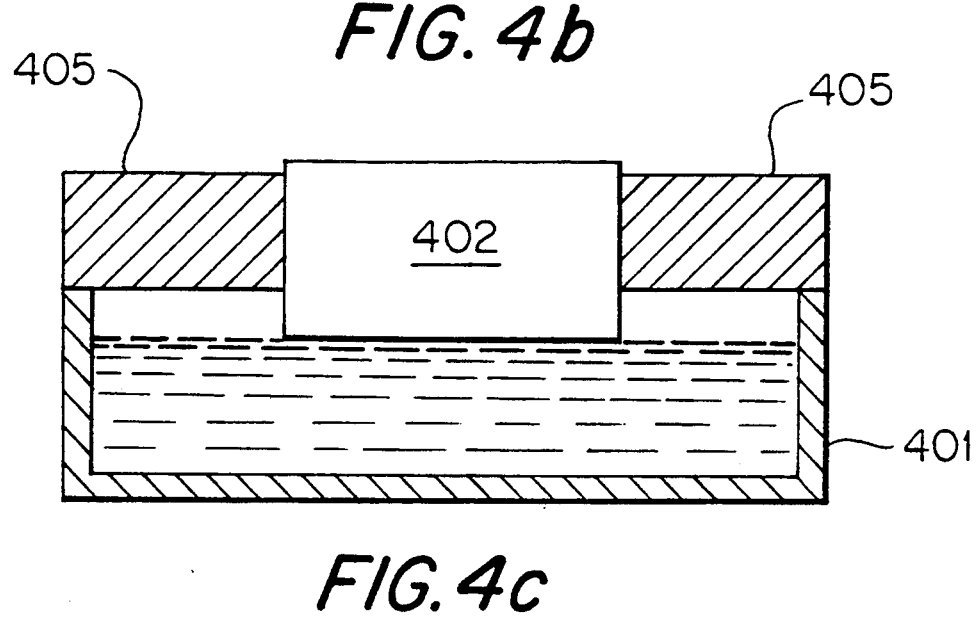

The three embodiments of the present invention described above used solid samples at room temperature. However, the present invention can be used with liquid samples by using, for example, sample holders fabricated from low thermal conductivity tubes (e.g., Nomex tubing obtained from M.Y. Keating). Alternatively, as shown in FIGS. 4a–4c, the liquid could be held in a crucible 401, with a metal specimen 402 of known thermal conductivity supported on thin, low-thermal-conductivity rods 403 in contact with the top surface of the liquid 404 (FIGS. 4a and 4b); or the liquid could be held in crucible 401, with a metal specimen 402 of known thermal conductivity supported by low thermal conductivity supports 405 on either side (FIG. 4c).

It can also be used at higher temperatures. At the higher temperatures, the dimensions of the samples can be measured, for example, by using equipment to measure the change in sample dimensions as a function of temperature. An apparatus for this measurement is the TMA 2940 Thermomechanical analyzer manufactured by TA Instruments, New Castle, Del. An alternative approach is to constrain the sample by holding it in clamps (without using a heat sink compound), such that its dimensions cannot change as a function of temperature. For best results, the clamps should be made from low-conductivity materials, to reduce the effect of the clamps on the measurement.

With high conductivity materials, shorter modulation periods, i.e., higher modulation frequencies, should be used, to ensure that the condition $e^{4\Lambda L} >> 1$ is maintained. Alternatively, the exact heat flow equation could be used.

Because the thermal conductivity measurements carried out according to the present invention are highly reproducible, calibration procedures can be used to further improve the measurement. Differential techniques can be used to subtract background effects, or to obtain relative measurements of thermal conductivity with greater accuracy.

EXAMPLES

The following examples are provided to illustrate certain embodiments of the present invention. They are not to be construed as limiting the invention in any way. The procedures described in the examples were performed using a TA Instruments 910 DSC cell and a 2910 base DSC (modified for MDSC), an MDSC cooling head placed on the 910 DSC cell, a liquid nitrogen cooling accessory ("LNCA") to supply liquid nitrogen to the MDSC cooling head, and a 2200 controller. The MDSC apparatus and method are described in the parent application. All measurements were performed at 30° C. with a temperature modulation amplitude of +/−1° C. and a modulation period of 80 seconds. The MDSC software analysis program was used to determine the heat capacity or specific heat from the respective runs. The modulation temperature amplitude was allowed to stabilize at the selected temperature ±1° C. before the data was used to compute the thermal conductivity.

EXAMPLE 1

Figure 2A:
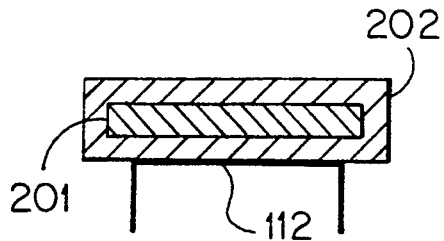
FIGS. 2a and 2b are schematic diagrams of the sample and reference configurations, respectively, used in the measurement of the bulk thermal conductivity of the encapsulated sample, as described in Example 1.
Figure 2B:
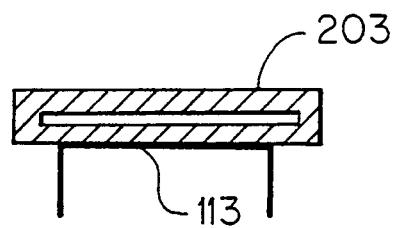

As shown in FIGS. 2a and 2b, 10.88 mg bead 201 of polystyrene ("PS"), randomly selected from a lot of PS beads obtained from Aldrich Chemical, was flattened at room temperature, using a small press. It was then encapsulated using a crimping press with a standard DSC aluminum pan and cover 202. A pan and cover of equal weight 203 was chosen and crimped in the same manner to provide an empty crimped pan for use as a reference, as shown in FIG. 2b. The 10.88 mg encapsulated sample was placed on the sample position 112 of the MDSC apparatus, and the empty crimped pan was placed on the reference position 113 of the MDSC apparatus. The heat capacity of the PS bead was then determined, as described above.

Figure 2C:
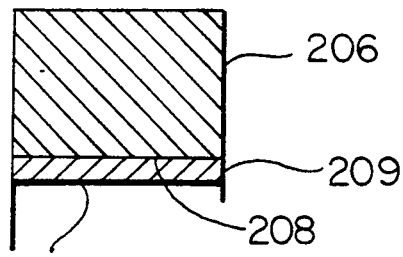
FIGS. 2c and 2d are schematic diagrams of the sample and reference configurations, respectively, used in the measurement of the bulk thermal conductivity of the unencapsulated sample, as described in Example 1.
Figure 2D:
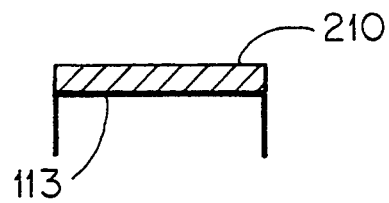

An unencapsulated sample from the same lot of PS was then fabricated in the form of a right angle circular cylinder as follows. An aluminum plate 0.307 cm thick was made with a series of 0.396 cm diameter holes. A flattened piece of aluminum foil was placed on the surface of a hot plate and the aluminum plate was placed on top of the foil. Beads of PS were then placed in the holes of the aluminum plate, a glass bell jar was placed over the aluminum plate, and the temperature of the hot plate was slowly increased until the PS softened and flowed. The bell jar was removed, and beads were then added to the holes, and the bell jar was replaced. This process was repeated until the holes were filled to over flowing with PS. The hot plate was then turned off and the aluminum plate was allowed to cool slowly. When the aluminum plate had cooled down, the aluminum foil was peeled from its back and the front and back surface of the aluminum plate were sanded until the PS in the holes was flush with the surfaces of the aluminum plate. The PS was then pressed out of the holes with a mandrel. The PS cylinders thus obtained were weighed and their dimensions measured. As shown in FIG. 2c, PS cylinder 206 was placed, as the unencapsulated sample, on the sample position 112 of the MDSC cell with its axis vertical. The flat face 208 of the unencapsulated sample was placed in good thermal contact with the sample position using a small amount of heat sink compound 209. An equal amount of the heat sink compound 210 was placed on the reference position 113 as shown in FIG. 2d. The unencapsulated sample was then run under the same conditions as the encapsulated sample. The heat capacity was then determined using MDSC following the procedures described in the parent application. The results of these measurements and determinations are as follows:

M=sample weight=39.70 mg
L=length of sample=0.307 cm
A=sample cross section area=0.123 cm$^2$
$\rho$=sample density=1.04 g/cm$^3$
$C_p$=sample specific heat(J/g °C.)=1.38
C=heat capacity(J/ °C.)=0.0241
$\omega$=angular frequency of modulation=0.0785 sec$^{-1}$ These values are substituted into the following equation to determine the sample heat capacity (K).

$$K = (\omega \cdot C^2)/(C_p \cdot \rho \cdot A^2)$$

The value of K obtained in this measurement was $21 \times 10^{-2}$ W/m °C., compared to the value reported in the literature of $14 \times 10^{-2}$ W/m °C.

EXAMPLE 2

The sample of example 1 was re-measured. The sample was removed from the cell. All heat sink compound was removed from the sample, from the sample position and from the reference position. The cleaned sample was now place on the sample position with the same side down. All parameters were the same with the exception of the heat capacity which was measured at 0.0220J/°C. The thermal conductivity was then calculated to be $18 \times 10^{-2}$ W/m °C.

EXAMPLE 3

Figure 2E:
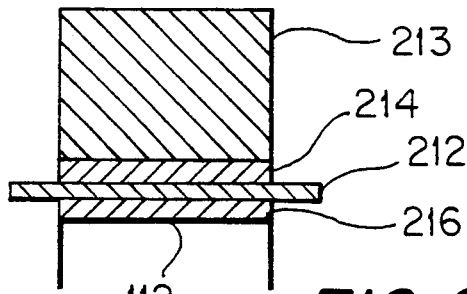
FIGS. 2e and 2f are schematic diagrams of the sample and reference configurations, respectively, used in the measurement of the thermal conductivity of bulk materials, when a heat sink compound and conducting foil is used to reduce spurious thermal resistance paths, as described in Example 3.
Figure 2F:
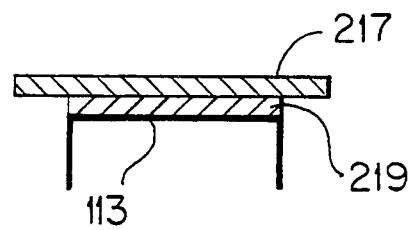

Using the procedure of example 1 the sample of PS was re-measured, using the mounting procedure shown in FIG. 2e. A 6 mm diameter disc of 2 mils thick aluminum foil 212 was attached to the bottom surface of sample 213 with a thin uniform layer of heat sink compound 214. The sample was pressed against the foil to remove excess heat sink compound. The sample was then attached to the sample position 112 with a thin layer of heat sink compound 216 between the bottom surface of the aluminum foil and the sample position mesa, by pressing the sample down. As shown in FIG. 2f, an identical disc 217 was also attached to the reference position 113 with heat sink compound 119, and pressed down with a flat tool. The same value of heat capacity was measured as in example 1.

EXAMPLE 4

Figure 2G:
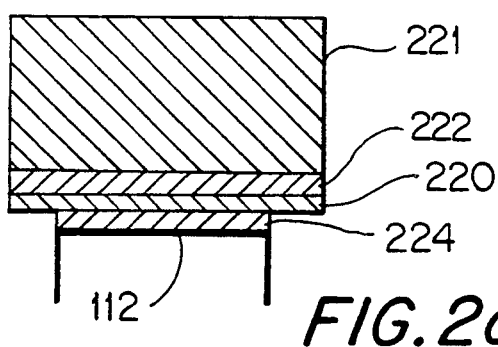
FIGS. 2g and 2h are schematic diagrams of the sample and reference configurations, respectively, used in the measurement of the thermal conductivity of bulk materials, when a heat sink compound and conducting foil is used to reduce spurious thermal resistance paths, as described in Example 4.
Figure 2H:
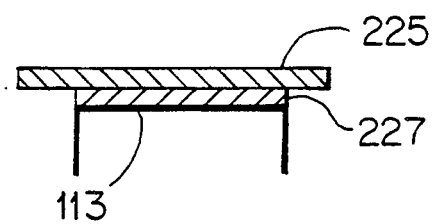

Using the procedure of example 3, a new sample 221 of PS was measured. As shown in FIG. 2g, a disc of aluminum foil 220 was attached to the bottom surface of sample 221 with a thin uniform layer of heat sink compound 222. Sample 221 was then attached to sample position 112 with a thin layer of heat sink compound 224 between the bottom surface of the aluminum foil 220 and the sample position mesa, by pressing the sample down. As shown in FIG. 2h, an identical disc 225 was also attached to the reference position 113 with heat sink compound 227, and pressed down with a flat tool. The diameter of this sample was 0.579 cm. The sample was prepared as in example 1, but the diameter of the holes in the aluminum plate was 0.579 cm. The following parameters were measured:

M = sample weight = 84.46 mg
L = length of sample = 0.307 cm
A = sample cross section area = 0.267 cm$^2$
$\rho$ = sample density = 1.04
$C_p$ = sample specific heat(J/g °C.) = 1.38
C = heat capacity(J/ °C.) = 0.0466
$\omega$ = angular frequency of modulation = 0.0785 sec$^{-1}$ Substituting into equation (1), K was calculated to be $17 \times 10^{-2}$ W/m °C.

EXAMPLE 5

A series of samples of different materials was run using the mounting procedures of Example 2. The measurement and analysis described in example 1 were followed. Table I lists these measurements as well as a series of measurements on PS.

TABLE I

COMPARATIVE RESULTS OF TC MEASUREMENTS
(UNITS: K = W/m°C. × 10$^{-2}$, length (L) = cm, diameter (D) = cm)

| Sample | L | D | K (cal) | K (lit) | % var | mean/% | Comments |
|---|---|---|---|---|---|---|---|
| PS | 0.307 | 0.578 | 17 | 14 | +21 | 17/2.2 | av. of 3 runs |
|  | " | " | 17 |  | +21 |  |  |
|  | " | " | 16 |  | +14 |  |  |
|  | " | " | 17 |  | +21 |  |  |
| Teflon | 0.325 | 0.357 | 37 | 34 | +12 | 36/2.3 |  |
|  | 0.404 | " | 36 |  | +9 |  |  |

TABLE I-continued

COMPARATIVE RESULTS OF TC MEASUREMENTS
(UNITS: K = W/m°C. × 10$^{-2}$, length (L) = cm, diameter (D) = cm)

| Sample | L | D | K (cal) | K (lit) | % var | mean/% | Comments |
|---|---|---|---|---|---|---|---|
|  | 0.508 | " | 35 |  | +6 |  |  |
| NA lime | 0.302 | 0.599 | 76 | 71 | +7 | 76/7.5 | av. of 3 runs |
|  | " | " | 67 |  | −6 |  |  |
|  | " | " | 85 |  | +20 |  |  |
| Pyrex 7740 | 0.384 | 0.578 | 118 | 110 | +7 | 112/4.7 |  |
|  | " | " | 108 |  | −2 |  |  |
|  | " | " | 117 |  | +6 |  |  |
|  | " | " | 106 |  | −5 |  |  |

EXAMPLE 6

A cell correction procedure was used on the thermal conductivity calculated values shown in Table I. As described above, this correction factor accounts for the excess heat flow measured in the cell due the ambient gas present. The basic procedure is to measure a sample with known thermal conductivity. Using the measured thermal conductivity and the known value obtained from the scientific literature a cell correction factor is applied to subsequently-measured samples. The samples are prepared with similar dimensions, and measured under the same conditions, to obtain a corrected value of thermal conductivity. The equation used is:

$$K_t = \frac{(K - 2C + \sqrt{K^2 - 4CK})}{2}$$

where
K = the measured thermal conductivity
$K_t$ = corrected thermal conductivity
C = the correction factor Using PS as the sample with known thermal conductivity, C was determined to be 1.43. The resulting corrected thermal conductivity values are shown in Table II, as well as the uncorrected values and the % error of these values from the literature values.

TABLE II

CORRECTED THERMAL CONDUCTIVITIES

| Sample | $K_m$ | $K_t$ | (K lit.) | % Error | % Error (Corr) |
|---|---|---|---|---|---|
| PS | 17 | 14 | 14 | 21 | "0" |
| Teflon | 37 | 34 | 33 | 12 | 3 |
| Na lime | 76 | 73 | 71 | 7 | 3 |
| Pyrex | 112 | 109 | 110 | 2 | 1 |

EXAMPLE 7

Figure 3A:
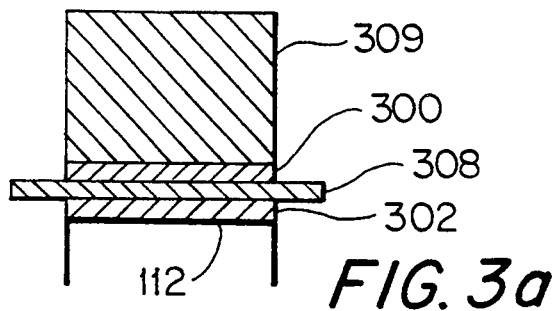
FIGS. 3a and 3b are schematic diagrams of the sample and reference configurations for the measurement of the thermal conductivity of thin films.
Figure 3B:
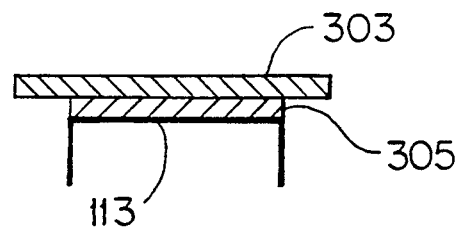

The thermal conductivity of a PET film 7.5 mil thick was measured using the configuration shown in FIGS. 3a and 3b. The heat capacity of an aluminum cylinder 309 0.401 cm in diameter and 0.312 cm long was measured as in example 1. Two 6 mm diameter PET discs were punched out of a sheet of PET 7.5 mils thick. One PET disc, shown as disc 303 in FIG. 3b, was attached with heat sink compound 305 to the reference position 113. The other PET disc, shown as disc 308 in FIG. 3a, was attached to sample position 112 using heat sink compound 302. The bottom surface of aluminum cylinder 309, as shown in FIG. 3a, was attached to the top surface of PET disc 308 with heat sink compound 300. The effective heat capacity of aluminum cylinder 309 was then measured. The thermal conductivity of the PET film was computed using the following equation.

$$K = \frac{\omega C_{true} L}{A} \left( \frac{1}{\left(\frac{C_{true}}{C_{eff}}\right)^2 - 1} \right)^{\frac{1}{2}}$$

where
$\omega$ = the angular frequency of the modulation = 0.0785 sec$^{-1}$;
L = the film thickness = 0.0191 cm;
A = the cross section of the aluminum cylinder = 0.126 cm$^2$;
$C_{true}$, the heat capacity of the aluminum cylinder directly attached to the sample position, is equal to 0.0989 J/°C.; and
$C_{eff}$, the heat capacity of the aluminum cylinder when attached to the sample position via the PET disc, is equal to 0.0776 J/°C.

Substituting these values into the above equation the resulting thermal conductivity is $15 \times 10^{-2}$ W/m °C. This compares to the value in the scientific literature of $14.7 \times 10^{-2}$ W/m °C.

The foregoing disclosure of embodiments of the present invention has been presented for purposes of illustration and description. It is not intended to be exhaustive or to limit the invention to the precise forms disclosed. Many variations and modifications of the embodiments described herein will be obvious to one of ordinary skill in the art in light of the above disclosure. The scope of the invention is to be defined only by the claims appended hereto, and by their equivalents.

What is claimed is:

1. A method for measuring the thermal conductivity of a material comprising:
   (a) preparing a first sample of the material in the form of a thin wafer having a known thickness, known dimensions and known weight;
   (b) encapsulating the first sample of the material in a thin layer of conforming high thermal conductivity material, the mass of said thin layer of high thermal conductivity material having a first value;
   (c) preparing a second sample of the material as a right angle cylinder having flat and parallel top and bottom surfaces, the height of said cylinder being greater than the thickness of the first sample of the material;
   (d) providing a differential scanning calorimeter having a sample position and a reference position, said differential scanning calorimeter comprising means for modulating the temperature of the sample and reference positions at selected modulation angular frequencies and modulation amplitudes;
   (e) placing the first sample in the sample position of the differential scanning calorimeter;
   (f) placing a thin wafer of the high thermal conductivity material on the reference position of the differential scanning calorimeter, the mass of said thin wafer of high thermal conductivity material having the first value;
   (g) measuring the effective heat capacity of the first sample by:
      ($\alpha$) selecting a modulation angular frequency and a modulation amplitude,
      ($\beta$) varying the temperature of the sample position and the reference position according to the selected modulation amplitude and modulation angular frequency, and
      ($\gamma$) recording a differential signal representative of differential changes in the heat flow to and from the sample position with respect to the heat flow to and from the reference position;
   (h) removing the first sample from the sample position;
   (i) removing the thin wafer of high thermal conductivity material from the reference position;
   (j) placing the second sample on the sample position of the differential scanning calorimeter;
   (k) measuring the effective heat capacity of the second sample by:
      ($\alpha$) selecting a modulation angular frequency and a modulation amplitude,
      ($\beta$) varying the temperature of the sample position and the reference position according to the selected modulation amplitude and modulation angular frequency, and
      ($\gamma$) recording a differential signal representative of differential changes in the heat flow to and from the sample position with respect to the heat flow to and from the reference position; and
   (l) calculating the thermal conductivity of the material from the measured heat capacities of the first sample and of the second sample, from the dimensions and weights of the first sample and of the second sample, and from the modulation angular frequency.

2. The method for measuring the thermal conductivity of a material of claim 1, wherein the thickness of the first sample is 1 mm or less.

3. The method for measuring the thermal conductivity of a material of claim 1, wherein heat sink compound is used as the encapsulating material.

4. The method for measuring the thermal conductivity of a material of claim 1, wherein the second sample is a circular right angle cylinder.

5. The method for measuring the thermal conductivity of a material of claim 1, wherein the first sample is a wafer in the form of a circular disc.

6. The method for measuring the thermal conductivity of a material of claim 1, further comprising allowing the modulation temperature amplitude to stabilize prior to measuring the heat capacity of the first sample in step (g), and prior to measuring the effective heat capacity of the second sample in step (k).

7. The method for measuring the thermal conductivity of a material of claim 1, wherein the second sample is mounted onto the sample position by attaching a first surface of a first wafer of metal foil to the second sample using high thermal conductivity material, and then attaching a second surface of the first wafer of metal foil to the sample position using high thermal conductivity material.

8. The method for measuring the thermal conductivity of a material of claim 7, further comprising attaching a second wafer of metal foil to the reference position, said second wafer having the same thickness and dimensions as the first wafer, said second wafer being made being made from the same material as the first wafer.

9. The method for measuring the thermal conductivity of a material of claim 8, wherein the high thermal conductivity material is heat sink compound.

10. The method for measuring the thermal conductivity of a material of claim 7, wherein the high thermal conductivity material is heat sink compound.

11. The method for measuring the thermal conductivity of a material of claim 1, further comprising:
   (m) selecting a known material having a known thermal conductivity;
   (n) preparing a sample of the known thermal conductivity material having dimensions similar to the dimensions of the second sample;
   (p) measuring the thermal conductivity of the sample of known thermal conductivity;
   (q) calculating a correction factor; and
   (r) calculating a corrected value of the thermal conductivity of the material.

12. The method for measuring the thermal conductivity of a material of claim 11, wherein the thickness of the first sample is 1 mm or less.

13. The method for measuring the thermal conductivity of a material of claim 11, wherein heat sink compound is used as the encapsulating material.

14. The method for measuring the thermal conductivity of a material of claim 11, wherein the second sample is a circular right angle cylinder;

15. The method for measuring the thermal conductivity of a material of claim 11, further comprising allowing the modulation temperature amplitude to stabilize prior to measuring the heat capacity of the first sample in step (g), and prior to measuring the effective heat capacity of the second sample in step (k).

16. A method for measuring the thermal conductivity of a thin film material comprising:
   (a) preparing a right angle cylinder of a material having a known heat capacity, said cylinder having flat and parallel top and bottom surfaces and having a known cross-sectional area;
   (b) preparing two wafers of the thin film material, said wafers having similar dimensions and thicknesses, and measuring the thickness of the two wafers;
   (c) providing a differential scanning calorimeter having a sample position and a reference position, said differential scanning calorimeter comprising means for modulating the temperature of the sample and reference positions at selected modulation angular frequencies and modulation amplitudes;
   (d) placing a layer of high thermal conductivity compound uniformly over the sample position of the differential scanning calorimeter;
   (e) placing an amount of the high thermal conductivity material over the reference position of the differential scanning calorimeter equal to the amount placed over the reference position;
   (f) mounting the cylinder on the same position of the differential scanning calorimeter;
   (g) selecting a modulation angular frequency and a modulation amplitude;
   (h) measuring the true heat capacity of the cylinder, using the selected modulation angular frequency and the selected modulation amplitude;
   (i) removing the cylinder from the sample position;
   (j) mounting one wafer of the thin film material onto the sample position, and the other wafer of the thin film material to the reference position;
   (k) mounting the cylinder of the known heat capacity material over the wafer on the sample position;
   (l) measuring the effective heat capacity of the cylinder using the selected modulation angular frequency and the selected modulation amplitude; and
   (m) calculating the thermal conductivity of the film from the true heat capacity of the cylinder measured in step (h), the effective heat capacity of the cylinder measured in step (l), the thickness of the thin films, the selected modulation angular frequency and the cross-sectional area of the cylinder.

17. The method for measuring the thermal conductivity of a thin film material of claim 16, wherein the cylinder has a circular cross-section.

18. The method for measuring the thermal conductivity of a thin film material of claim 16, wherein the two wafers are circular discs.

19. The method for measuring the thermal conductivity of a thin film material of claim 16, wherein the cylinder is a metal cylinder.

20. The method for measuring the thermal conductivity of a thin film material of claim 19, wherein the metal cylinder is an aluminum metal cylinder.

21. The method for measuring the thermal conductivity of a thin film material of claim 16, wherein the high conductivity material is heat sink compound.

22. A method for measuring the thermal conductivity of a material comprising:
   (a) preparing a sample of the material as a right angle cylinder having flat and parallel top and bottom surfaces, the height of said cylinder being greater than 1 mm;
   (b) measuring the height of the cylinder, the dimensions of its cross-section, and the weight of the cylinder;
   (c) providing a differential scanning calorimeter having a sample position and a reference position, said differential scanning calorimeter comprising means for modulating the temperature of the sample and reference positions at selected modulation frequencies and modulation amplitudes;
   (d) placing the sample of the material on the sample position of the differential scanning calorimeter;
   (e) measuring a first effective heat capacity of the sample by:
      ($\alpha$) selecting a first modulation angular frequency and a first modulation amplitude;
      ($\beta$) varying the temperature of the sample position and the reference position according to the selected first modulation amplitude and first modulation angular frequency; and
      ($\gamma$) recording a differential signal representative of differential changes in the heat flow to and from the sample position with respect to the heat flow to and from the reference position;
   (f) measuring a second effective heat capacity of the sample by:
      ($\alpha$) selecting a second modulation angular frequency differing from the first modulation angular frequency by at least a factor of two,
      ($\beta$) selecting a second modulation amplitude,
      ($\gamma$) varying the temperature of the sample position and the reference position according to the selected second modulation amplitude and second modulation angular frequency, and
      ($\delta$) recording a differential signal representative of differential changes in the heat flow to and from the sample position with respect to the heat flow to and from the reference position; and
   (g) calculating the thermal conductivity of the material from the first and second effective measured heat capacities of the sample, from the height and cross-sectional dimensions of the cylinder, from the weight of the sample, and from the first and second angular modulation frequencies.

23. The method for measuring the thermal conductivity of a material of claim 22, wherein the second angular frequency is selected such that $e^{4\Lambda L}$ is not much greater than 1.

24. The method for measuring the thermal conductivity of a material of claim 22, wherein the cylinder has a circular cross-section.

25. The method for measuring the thermal conductivity of a material of claim 22, further comprising allowing the modulation temperature amplitude to stabilize prior to measuring the first effective heat capacity of the sample in step (e), and prior to measuring the second effective heat capacity of the sample in step (f).

26. A method for measuring the thermal conductivity of a material comprising:
   (a) providing a modulated differential scanning calorimeter having a sample position and a reference position, said modulated differential scanning calorimeter comprising means for modulating the temperature of the sample and reference positions at selected modulation angular frequencies and modulation amplitudes;
   (b) measuring the heat capacity of a sample of the material placed in the sample position in the modulated differential scanning calorimeter by measuring the differential heat flow to the sample position with respect to the reference position under quasi-ideal conditions;
   (c) measuring the effective heat capacity of a sample of the material in the modulated differential scanning calorimeter by measuring the differential heat flow to the sample position with respect to the reference position under non-ideal conditions; and
   (d) calculating the thermal conductivity of the material from the sample dimensions, sample weights, heat capacity measured under quasi-ideal conditions, and effective heat capacity measured under non-ideal conditions.

27. The method for measuring the thermal conductivity of a material of claim 26, wherein the sample in step (c) is the same sample as the sample in step (b), and the heat capacity measurement is carried out in step (b) at a first modulation angular frequency, and the heat capacity measurement in step (c) is carried out at a second modulation angular frequency.

28. The method for measuring the thermal conductivity of a material of claim 26, wherein the sample in step (c) is the same as the sample in step (b), and the heat capacity measurement is carried out in step (b) at a first modulation amplitude, and the heat capacity measurement in step (c) is carried out at a second modulation amplitude.

29. The method for measuring the thermal conductivity of a material of claim 26, wherein the sample in step (b) is a small sample encapsulated in high-conductivity material, and the sample in step (c) is a large unencapsulated sample.

30. The method for measuring the thermal conductivity of a material of claim 26, further comprising allowing the modulation temperature amplitude to stabilize prior to measuring the heat capacity of a sample in step (b), and prior to measuring the effective heat capacity of a sample in step (c).

31. The method for measuring the thermal conductivity of a material of claim 26, further comprising:
   (e) selecting a known material having a known thermal conductivity;
   (f) preparing samples of the known thermal conductivity material having dimensions similar to the dimensions of the samples used in steps (b) and (c);
   (g) measuring the thermal conductivity of the sample of known thermal conductivity;
   (h) calculating a correction factor from the measured thermal conductivity measured in step (g) and the known thermal conductivity; and
   (i) calculating a corrected value of the thermal conductivity of the material from the correction factor calculated in step (h) and the thermal conductivity calculated in step (d).

32. A method for measuring the thermal conductivity of a thin film material comprising:
   (a) providing a modulated differential scanning calorimeter having a sample position and a reference position, said modulated differential scanning calorimeter comprising means for modulating the temperature of the sample and reference positions at selected modulation angular frequencies and modulation amplitudes;
   (b) placing a sample of the thin film material on the sample position, and a matching sample of the thin film material on the reference position;
   (c) placing a specimen having a known heat capacity on top of the sample of the thin film on the sample position;
   (d) measuring the effective heat capacity of the specimen; and
   (e) calculating the thermal conductivity of the material from the dimensions and thickness of the sample of thin film material, from the dimensions and weight of the specimen, from the known heat capacity of the specimen, and from the effective heat capacity of the specimen measured in step (d).

33. A method for measuring the thermal conductivity of a thin film material comprising:
   (a) providing a modulated differential scanning calorimeter having a sample position and a reference position, said modulated differential scanning calorimeter comprising means for modulating the temperature of the sample and reference positions at selected modulation angular frequencies and modulation amplitudes;
   (b) placing a specimen on the sample position of the modulated differential scanning calorimeter;
   (c) measuring the true heat capacity of the specimen in the modulated differential scanning calorimeter under quasi-ideal conditions;
   (d) removing the specimen from the sample position;
   (e) placing a sample of the thin film material on the sample position, and a matching sample of the thin film material on the reference position;
   (f) placing the specimen on top of the sample of the thin film on the sample position;
   (g) measuring the effective heat capacity of the specimen; and
   (h) calculating the thermal conductivity of the material from the dimensions and thickness of the sample of thin film material, from the dimensions and weight of the specimen, from the true heat capacity measured in step (c), and from the effective heat capacity measured in step (g).

34. A method for measuring the thermal conductivity of a liquid material comprising:
   (a) providing a modulated differential scanning calorimeter having a sample position and a reference position, said modulated differential scanning calorimeter comprising means for modulating the temperature of the sample and reference positions at selected modulation angular frequencies and modulation amplitudes;

(b) placing a crucible containing a sample of the liquid material on the sample position, and a matching crucible containing a matching sample of the liquid material on the reference position;

(c) placing a specimen having a known heat capacity on top of the sample of the liquid material at the sample position, said specimen being supported by a plurality of low-conductivity rods;

(d) measuring the effective heat capacity of the specimen; and (e) calculating the thermal conductivity of the material from the depth of the liquid material in the crucible, the dimensions of the crucible, from the dimensions and weight of the specimen, from the known heat capacity of the specimen, and from the effective heat capacity of the specimen measured in step (d).

* * * * *